US00PP28902P3

(12) United States Plant Patent
Gass

(10) Patent No.: US PP28,902 P3
(45) Date of Patent: Jan. 30, 2018

(54) ***CHILOPSIS* PLANT NAMED 'MSWNLOPUR'**

(50) Latin Name: *Chilopsis linearis*
Varietal Denomination: MSWNLopur

(71) Applicant: Ronald E. Gass, Glendale, AZ (US)

(72) Inventor: Ronald E. Gass, Glendale, AZ (US)

(73) Assignee: Camelot Nurseries Inc., Glendale, AZ (US)

( * ) Notice: Subject to any disclaimer, the term of this patent is extended or adjusted under 35 U.S.C. 154(b) by 45 days.

(21) Appl. No.: 14/999,470

(22) Filed: May 11, 2016

(65) Prior Publication Data

US 2017/0332534 P1 Nov. 16, 2017

(51) Int. Cl.
*A01H 5/00* (2006.01)

(52) U.S. Cl.
USPC ..... Plt./216

(58) Field of Classification Search
USPC ..... Plt./226, 216
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Chilopsis* plant named 'MSWNLopur', characterized by its upright to somewhat outward plant habit; moderately vigorous growth habit; numerous relatively small leaves; freely flowering habit; and dark purple-colored flowers that typically do not produce fruits and seeds.

1 Drawing Sheet

Botanical designation: *Chilopsis linearis*.
Cultivar denomination: 'MSWNLopur'.

BACKGROUND OF THE INVENTION

The present invention relates to a new and distinct cultivar of *Chilopsis* plant, commonly referred to as Desert Willow, botanically known as *Chilopsis linearis* and hereinafter referred to by the name 'MSWNLopur'.

The new *Chilopsis* plant is a product of a planned breeding program conducted by the Inventor in Glendale, Ariz. The objective of the breeding program is to create new early and freely flowering *Chilopsis* plants with attractive flower coloration.

The new *Chilopsis* plant originated from an open-pollination in Glendale, Ariz. of an unnamed selection of *Chilopsis linearis*, not patented, as the female, or seed parent with an unknown selection of *Chilopsis linearis* as the male, or pollen, parent. The new *Chilopsis* plant was discovered and selected by the Inventor as a single flowering plant from within the progeny of the stated open-pollination in a controlled environment in Glendale, Ariz. in June, 2004.

Asexual reproduction of the new *Chilopsis* plant by cuttings in Glendale, Ariz. since April, 2011 has shown that the unique features of this new *Chilopsis* plant are stable and reproduced true to type in successive generations.

SUMMARY OF THE INVENTION

Plants of the new *Chilopsis* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MSWNLopur'. These characteristics in combination distinguish 'MSWNLopur' as a new and distinct *Chilopsis* plant:

1. Upright to somewhat outward plant habit.
2. Moderately vigorous growth habit.
3. Numerous relatively small leaves.
4. Freely flowering habit.
5. Dark purple-colored flowers that typically do not produce fruits and seeds.

Plants of the new *Chilopsis* can be compared to plants of the female parent selection. Plants of the new *Chilopsis* differ primarily from plants of the female parent selection in the following characteristics:

1. Plants of the new *Chilopsis* are fuller and more rounded than plants of the female parent selection.
2. Plants of the new *Chilopsis* are more densely foliated than plants of the female parent selection.
3. Leaves of plants of the new *Chilopsis* are smaller and darker green in color than plants of the female parent.
4. Plants of the new *Chilopsis* and the female parent selection differ in flower color as plants of the female parent selection have flowers that are white and pink to purple in color.
5. Plants of the new *Chilopsis* rarely produce fruits and seeds whereas plants of the female parent selection typically produce fruits and seeds.

Plants of the new *Chilopsis* can be compared to plants of *Chilopsis linearis* 'Art's Seedless', not patented. Plants of the new *Chilopsis* differ primarily from plants of 'Art's Seedless' in flower color as plants of 'Art's Seedless' have rose pink-colored flowers.

Plants of the new *Chilopsis* can be compared to plants of *Chilopsis linearis* 'Lucretia Hamilton', not patented. Plants of the new *Chilopsis* differ primarily from plants of 'Lucretia Hamilton' in flower color as plants of 'Lucretia Hamilton' have deep pink to purple-colored flowers.

BRIEF DESCRIPTION OF THE PHOTOGRAPHS

The accompanying colored photographs illustrate the overall appearance of the new *Chilopsis* plant showing the colors as true as it is reasonably possible to obtain in colored reproductions of this type. Colors in the photographs may differ slightly from the color values cited in the detailed botanical description which accurately describe the actual colors of the new *Chilopsis* plant.

The photograph at the top of the sheet comprises a side perspective view of a typical flowering plant of 'MSWN-Lopur' grown in a container.

The photographs at the bottom of the sheet are close-up views of typical leaves, flower buds and flowers of 'MSWN-Lopur'.

DETAILED BOTANICAL DESCRIPTION

The aforementioned photographs and following observations, measurements and values describe plants grown during the spring in five-gallon containers in an outdoor nursery in Glendale, Ariz. and under cultural practices typical of commercial *Chilopsis* production. During the production of the plants, day temperatures ranged from 26° C. to 41° C. and night temperatures ranged from 26° C. to 30° C. Plants were 2.5 years old when the photographs and detailed description were taken. In the following description, color references are made to The Royal Horticultural Society Colour Chart, 2007 Edition, except where general terms of ordinary dictionary significance are used.

Botanical classification: *Chilopsis linearis* 'MSWNLopur'.

Parentage:

- *Female, or seed, parent*.—Unnamed selection of *Chilopsis linearis*, not patented.
- *Male, or pollen, parent*.—Unknown selection of *Chilopsis linearis*, not patented.

Propagation:

- *Type*.—By vegetative cuttings.
- *Time to initiate roots, summer*.—About three weeks at soil temperatures about 27° C.
- *Time to produce a rooted young plant, summer*.—After root initiation, about three weeks at soil temperatures about 27° C.
- *Root description*.—Medium in thickness; fibrous; white in color.
- *Rooting habit*.—Freely branching; medium density.

Plant description:

- *Plant and growth habit*.—Small tree, perennial; upright to somewhat outward plant habit; overall, oval in shape; moderately vigorous growth habit.
- *Plant height*.—About 132 cm.
- *Plant width (or plant spread)*.—About 54 cm.
- *Lateral branch description*.—Branching habit: Freely branching habit with typically two primary branches each with about 12. to 15 secondary branches. Length: About 15 cm to 78 cm depending on position. Diameter: About 1.3 cm to 2.6 cm. Internode length: About 5 mm to 10 mm. Strength: Strong. Aspect: Primary branches, mostly upright; secondary branches, about 45 to 55° from vertical. Texture and luster, developing: Sparsely pubescent; semi-glossy. Texture and luster, developed: Woody, glabrous; matte. Color, developing: Close to 146D. Color, developed: Close to 201A to 201B.

Leaf description:

- *Arrangement*.—Opposite; simple.
- *Length*.—About 7.8 cm.
- *Width*.—About 1.2 cm.
- *Shape*.—Narrowly lanceolate.
- *Apex*.—Acute to acuminate.
- *Base*.—Attenuate.
- *Margin*.—Entire.
- *Texture and luster, upper and lower surfaces*.—Smooth, glabrous; glossy.
- *Venation pattern*.—Arcuate.
- *Color*.—Developing leaves, upper and lower surfaces: Close to 146C. Fully expanded leaves, upper surface: Close to 146A; venation, close to 146A to 146B. Fully expanded leaves, lower surface: Close to 146B; venation, close to 146D.
- *Petioles*.—Length: About 3 mm. Diameter: About 1 mm. Strength: Moderately strong. Texture and luster, upper and lower surfaces: Smooth, glabrous; slightly glossy. Color, upper and lower surfaces: Close to 146D.

Flower description:

- *Flower form and flowering habit*.—Single two-lipped tubular flowers arranged in short and loose terminal racemes; flowers face mostly outwardly to slightly drooping; freely flowering habit with about eight to ten flowers per inflorescence and about 75 to 80 flowers developing per plant.
- *Natural flowering season*.—Plants flower during the spring and summer in Arizona.
- *Flower longevity*.—Flowers last about four days on the plant; flowers not persistent.
- *Fragrance*.—None detected.
- *Inflorescence height*.—About 3 cm.
- *Inflorescence diameter*.—About 6.3 cm.
- *Flower buds*.—Height: About 3.2 cm. Diameter: About 1.1 cm. Shape: Elongate. Texture and luster: Smooth, glabrous; matte. Color: Close to N79A to N79B.
- *Flowers*.—Appearance: Salverform; flared trumpet, corolla fused and two-lipped. Diameter: About 3 cm by 3.5 cm. Length: About 4.6 cm. Throat diameter: About 8 mm by 12 mm. Tube length: About 2.7 cm. Tube diameter: Proximally, about 3 mm; distally, about 12 mm.
- *Corolla*.—Quantity and arrangement: Five petals arranged in a single whorl and fused towards the base into an elongated tube with flared petal lobes. Petal lobe length: About 1.5 cm. Petal lobe width: About 1.2 cm to 1.5 cm. Petal lobe shape: Orbicular. Petal lobe apex: Rounded. Petal lobe margin: Erose and somewhat sinuate; undulate. Petal lobe texture and luster, upper surface: Smooth, velvety; matte. Petal lobe texture and luster, lower surface: Smooth, glabrous; matte. Throat texture: Smooth, slightly pubescent along lower lip. Tube texture: Mostly smooth, glabrous; longitudinally ridged along base of tube. Color: Petal lobe, when opening, upper surface: Close to N79A. Petal lobe, when opening, lower surface: Close to N79B. Petal lobe, fully opened, upper surface: Close to N79A to N79B; venation, close to N79B; color does not change with subsequent development. Petal lobe, fully opened, lower surface: Close to N79A; venation, close to N79B; color does not change with subsequent development. Throat: Close to N79C to N79D; proximally, close to 85D; thin (about 1 mm wide) stripes on lower lip, close to 161B; venation, close to N79B. Tube: Proximally, close to 84C; mid-section, close to N77D; distally, close to N79D; venation, close to N77B.

*Calyx*.—Quantity and arrangement: Two sepals, opposite; fused at the base. Sepal length: About 1.2 mm. Sepal width: About 4.5 mm. Sepal shape: Elliptical. Sepal apex: Acute to acuminate. Sepal margin: Entire. Sepal texture and luster, upper and lower surfaces: Pubescent; matte. Sepal color: When developing and fully opened, upper surface: Close to 155A. When developing and fully opened, lower surface: Close to 155D.

*Peduncles*.—Length: About 1.4 cm. Diameter: About 2 mm. Strength: Strong. Aspect: Mostly upright. Texture and luster: Minute pubescence; matte. Color: Close to 145A.

*Pedicels*.—Length: About 4 mm. Diameter: About 1.5 mm. Strength: Strong. Aspect: About 45° from peduncle axis. Texture and luster: Minute pubescence; matte. Color: Close to 145B.

*Reproductive organs*.—Stamens: Quantity per flower: Five total; typically four are functional and one is rudimentary. Filament length: About 1.2 cm. Filament color: Close to NN155D. Anther shape: Lanceolate. Anther size: About 2 mm by 4 mm. Anther color: Close to 161D. Pollen amount: Scarce. Pollen color: Close to 161D. Pistils: Quantity: Typically one. Pistil length: About 2.5 cm. Style length: About 2 cm. Style color: Close to NN155C to NN155D. Stigma diameter: About 1 mm. Stigma shape: Rounded and pointy. Stigma color: Close to NN155B. Ovary color: Close to 160C.

*Seeds and fruits*.—Seed and fruit production have not been observed on plants of the new *Chilopsis*.

Disease & pest tolerance: Plants of the new *Chilopsis* have been observed to have good tolerance to pathogens and pests common to *Chilopsis* plants.

Garden performance: Plants of the new *Chilopsis* have been observed to tolerate wind, rain and temperatures ranging from about −18° C. to about 46° C.

It is claimed:

1. A new and distinct *Chilopsis* plant named 'MSWN-Lopur' as illustrated and described.

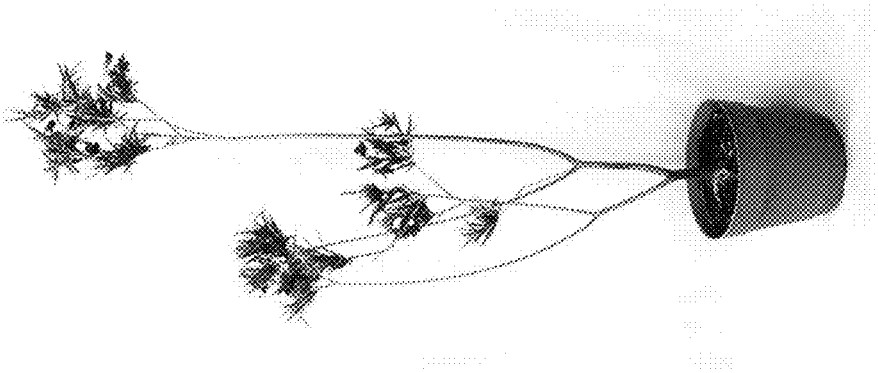
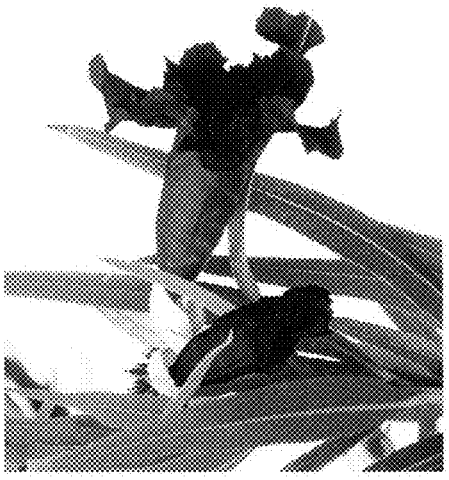
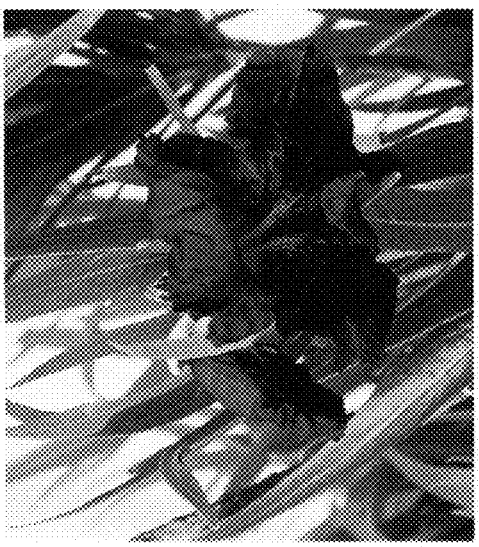

* * * * *